US009278191B2

(12) United States Patent
Nihonmatsu et al.

(10) Patent No.: US 9,278,191 B2
(45) Date of Patent: Mar. 8, 2016

(54) CATHETER

(71) Applicant: ASAHI INTECC CO., LTD., Nagoya-shi, Aichi (JP)

(72) Inventors: Masaaki Nihonmatsu, Kasugai (JP); Yukiko Enami, Seto (JP)

(73) Assignee: ASAHI INTECC CO., LTD., Nagoya (JP)

( * ) Notice: Subject to any disclaimer, the term of this patent is extended or adjusted under 35 U.S.C. 154(b) by 0 days.

(21) Appl. No.: 14/643,252

(22) Filed: Mar. 10, 2015

(65) Prior Publication Data

US 2015/0265798 A1 Sep. 24, 2015

(30) Foreign Application Priority Data

Mar. 20, 2014 (JP) ................. 2014-057791

(51) Int. Cl.
*A61M 25/00* (2006.01)
(52) U.S. Cl.
CPC .......... *A61M 25/005* (2013.01); *A61M 25/0041* (2013.01)
(58) Field of Classification Search
CPC .......... A61M 25/005; A61M 25/0012; A61M 25/0053; A61M 25/0054; A61M 2025/09083; A61M 2025/09191
USPC ................... 600/585; 604/523–527
See application file for complete search history.

(56) References Cited

U.S. PATENT DOCUMENTS

| 4,169,464 A | 10/1979 | Obrez |
| 5,306,252 A * | 4/1994 | Yutori et al. ........... 600/585 |
| 5,526,849 A * | 6/1996 | Gray ........................ 138/133 |
| 6,689,120 B1 * | 2/2004 | Gerdts ....................... 604/526 |
| 7,104,979 B2 * | 9/2006 | Jansen et al. ............... 604/525 |
| 8,246,603 B2 | 8/2012 | Takagi et al. |
| 2001/0027310 A1 | 10/2001 | Parisi et al. |
| 2001/0047165 A1 * | 11/2001 | Makower ............... A61B 8/12 604/528 |
| 2003/0191451 A1 * | 10/2003 | Gilmartin .................. 604/527 |
| 2004/0002727 A1 * | 1/2004 | Hwang et al. ............... 606/194 |
| 2004/0243102 A1 * | 12/2004 | Berg et al. .................. 604/525 |
| 2009/0227932 A1 * | 9/2009 | Herrig ............... A61M 1/3653 604/6.16 |
| 2010/0130996 A1 * | 5/2010 | Doud ............ A61B 17/320783 606/159 |
| 2011/0071503 A1 | 3/2011 | Takagi et al. |
| 2014/0031796 A1 * | 1/2014 | Nishigishi et al. ........... 604/527 |
| 2014/0114287 A1 * | 4/2014 | Beasley et al. ............... 604/525 |

(Continued)

FOREIGN PATENT DOCUMENTS

| EP | 0732117 B1 | 8/1999 |
| EP | 2 692 388 A1 | 2/2014 |

(Continued)

OTHER PUBLICATIONS

Jul. 20, 2015 Extended European Search Report issued in European Application No. 15159469.4.

*Primary Examiner* — Gerald Landry, II
(74) *Attorney, Agent, or Firm* — Oliff PLC

(57) ABSTRACT

A catheter includes a catheter shaft having a body portion and a bend that extends distally from a distal end of the body portion. In the catheter, a braid is embedded in the catheter shaft. The braid has a first wire and a second wire woven together. The first wire has a high tensile strength and the second wire has a low tensile strength that is lower than the high tensile strength of the first wire. When viewed from a proximal end of the catheter shaft, the bend forms an arc that extends in a winding direction of the first wire.

6 Claims, 13 Drawing Sheets

(56) References Cited

U.S. PATENT DOCUMENTS

2014/0214006 A1* 7/2014 Hiroshige et al. ............ 604/527
2015/0100043 A1* 4/2015 Govari et al. ................ 604/528

FOREIGN PATENT DOCUMENTS

| EP | 2 695 635 A1 | 2/2014 |
| JP | 2011-083596 A | 4/2011 |

* cited by examiner

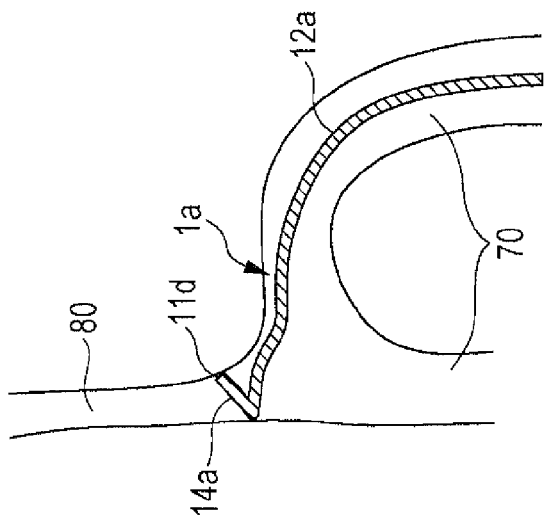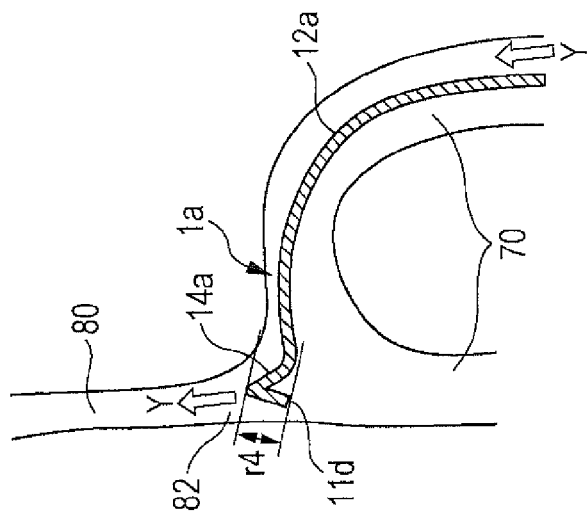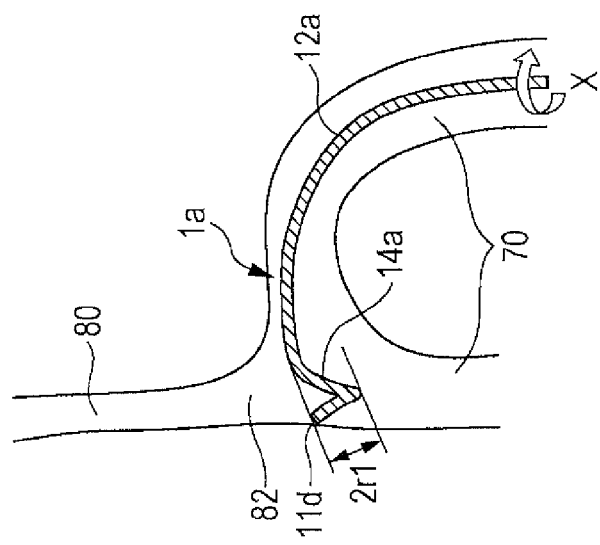

a bifurcation. US 9,278,191 B2

CATHETER

CROSS REFERENCE TO RELATED APPLICATION

This application claims priority to Japanese Patent Application No. 2014-057791 filed in the Japan Patent Office on Mar. 20, 2014, the entire contents of which are incorporated herein by reference.

BACKGROUND

The disclosed embodiments relate to a medical device. Specifically, the disclosed embodiments relate to a catheter that is capable of easily changing a proceeding direction from a major canal (a main branch) to a minor canal (a side branch) at a bifurcation.

When a stenosis site or an occlusion site is formed in a tubular organ such as a blood vessel, a bile duct, a pancreatic duct, or the like, the flow of fluid (e.g., blood, bile (biliary fluid), pancreatic juice, or the like) through the tubular organ becomes restricted. As a method of treating the stenosis site or the occlusion site, a treatment method using a catheter has been widely used.

Generally, the number of bifurcations of the major canal and minor canals of a tubular organ increases toward the end portion of the tubular organ. Accordingly, when a stenosis site or an occlusion site is formed at an end portion of a tubular organ, the catheter must be able to easily change its proceeding direction from a major canal (a main branch) to a minor canal (a side branch) at a bifurcation.

To address the above considerations, a known catheter includes a bend at a distal end of a catheter shaft in which the bend is bent obliquely towards a predetermined direction (see Japanese Patent Application Publication No. 2011-83596, for example). By providing such a bend, the distal end of the catheter can be oriented towards a direction that is offset with respect to a plane of the body portion of the catheter shaft.

However, in the catheter of Japanese Patent Application Publication No. 2011-83596, a braid is embedded into the catheter shaft, and includes a first wire and a second wire woven together and having the same wire diameter. Thus, the tensile strength of the first wire and the second wire are the same. Accordingly, regardless of whether a technician rotates the catheter in the clockwise direction or in the counterclockwise direction, the rotational force (torque) transmitted to the distal end of the catheter is the same. In other words, the rotational force is isotropic. With such a catheter, when the distal end of the catheter fails to enter a minor canal and is caught by a portion around the entrance of the minor canal at a bifurcation, the bend of the catheter shaft cannot be deformed when the technician rotates the catheter because the rotational force is isotropic. Accordingly, the distal end of the catheter cannot be easily inserted into the minor canal, and it takes time to change the proceeding direction of the catheter from the major canal to the minor canal.

SUMMARY

The disclosed embodiments have been devised in view of the above circumstances and aim to provide a catheter that can easily change the proceeding direction from a major canal to a minor canal of a bifurcation even when the distal end of the catheter is caught by a portion around the entrance of the minor canal.

The above problems are addressed by the following devices.

The disclosed embodiments include a catheter having a catheter shaft with a body portion and a bend that extends from the body portion towards a distal end of the catheter shaft. In the catheter, a braid is embedded in the catheter shaft. A first wire that has a high tensile strength and a second wire that has a low tensile strength (compared to the first wire) are woven together to form the braid, and when viewed from a proximal end of the catheter shaft, the bend forms an arc that extends in a winding direction of the first wire.

Since the tensile strength of the first wire is higher than the tensile strength of the second wire, when the technician rotates the catheter in the winding direction of the first wire, the properties of the braid are governed by the first wire, which functions as a coil. Accordingly, even when the distal end of the catheter is caught by a portion around the entrance of the minor canal at a bifurcation, the technician can deform the bend of the catheter shaft into a thin state by rotating the catheter in the winding direction of the first wire, thereby tightening the first wire. Accordingly, it is easy to change the proceeding direction of the catheter from the major canal to the minor canal, and the amount of time taken to insert the catheter into a stenosis site or an occlusion site formed at the end portion of a tubular organ is reduced.

Note that a portion of an outer layer and a portion of a braid are not shown for convenience of description.

Figure 2:
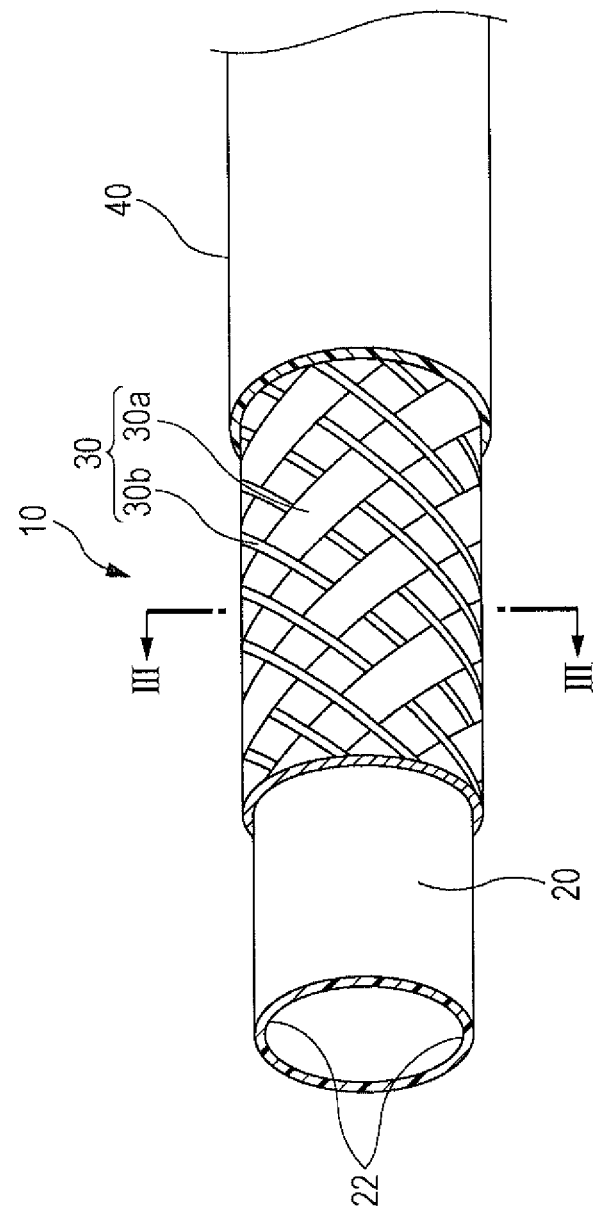
FIG. 2 is a diagram illustrating a catheter shaft of the catheter of FIG. 1.
Figure 3:
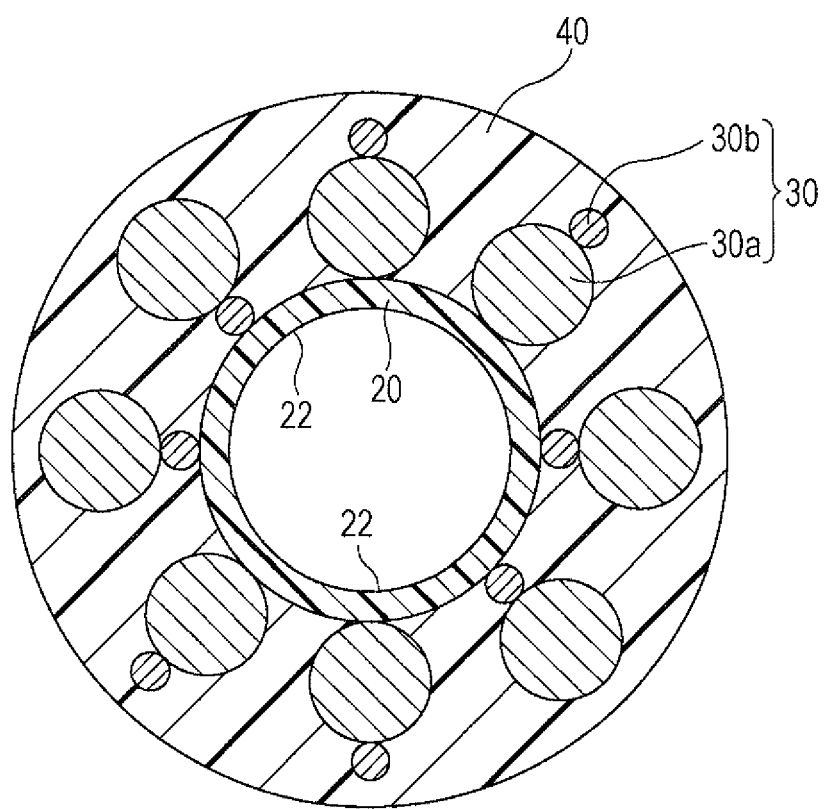

FIG. 3 is a cross-sectional view taken along line III-III of FIG. 2.

Figure 1:
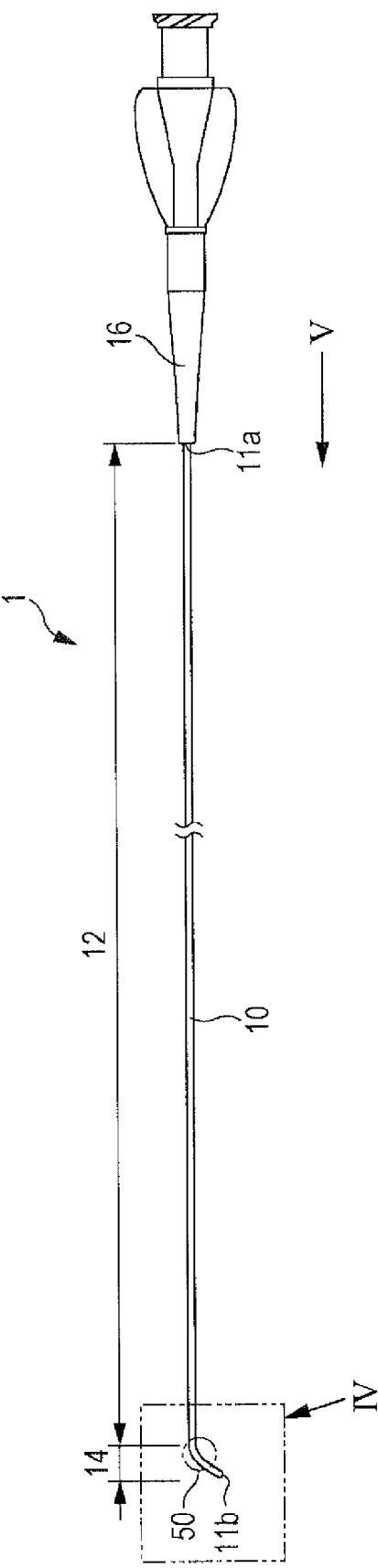
FIG. 1 is a general view of a catheter of the disclosed embodiments.
Figure 4:
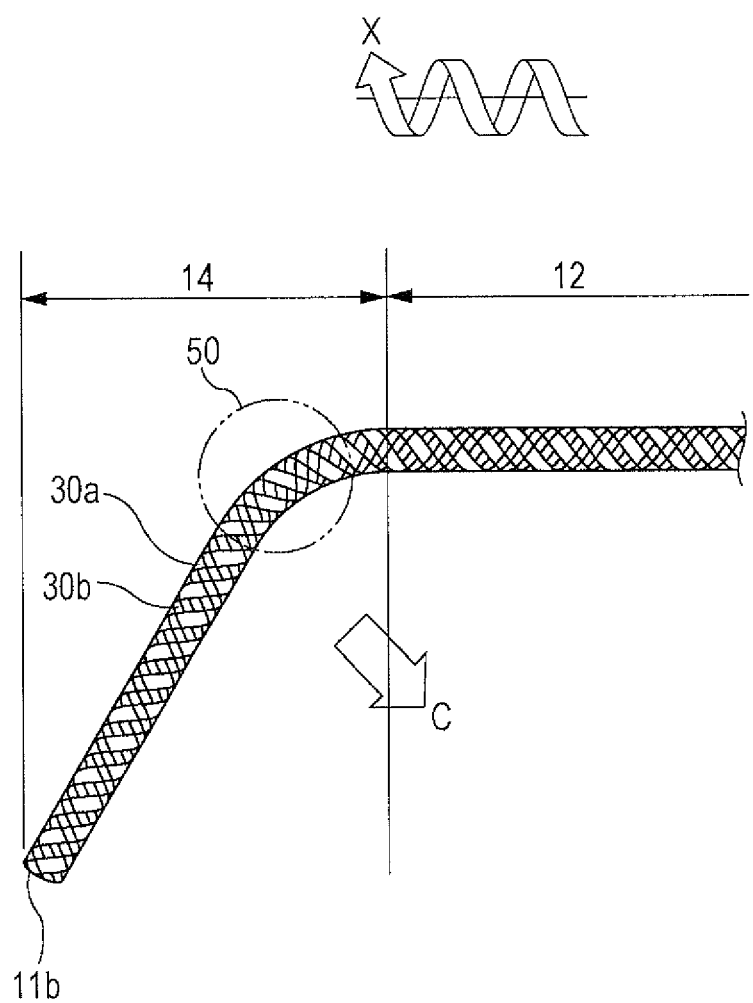

FIG. 4 is an enlarged diagram of portion IV of FIG. 1.

Figure 5:
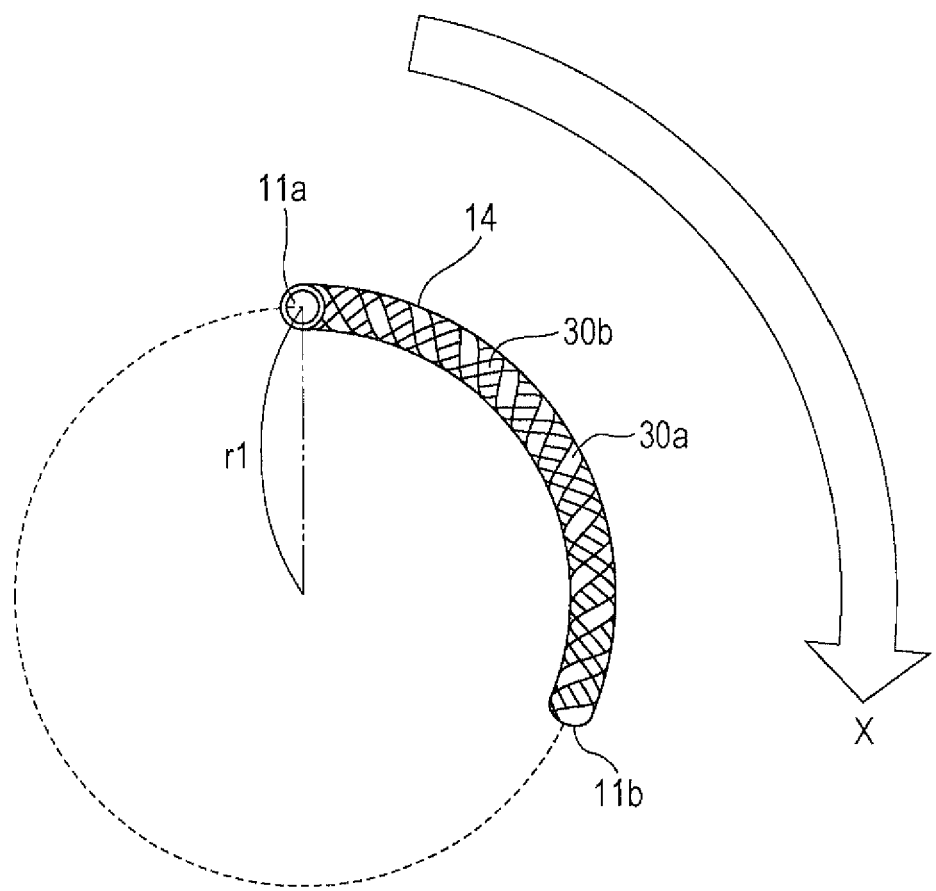

FIG. 5 is a diagram of the catheter shaft of FIG. 1 viewed from a proximal end of the catheter shaft.

Figure 6:
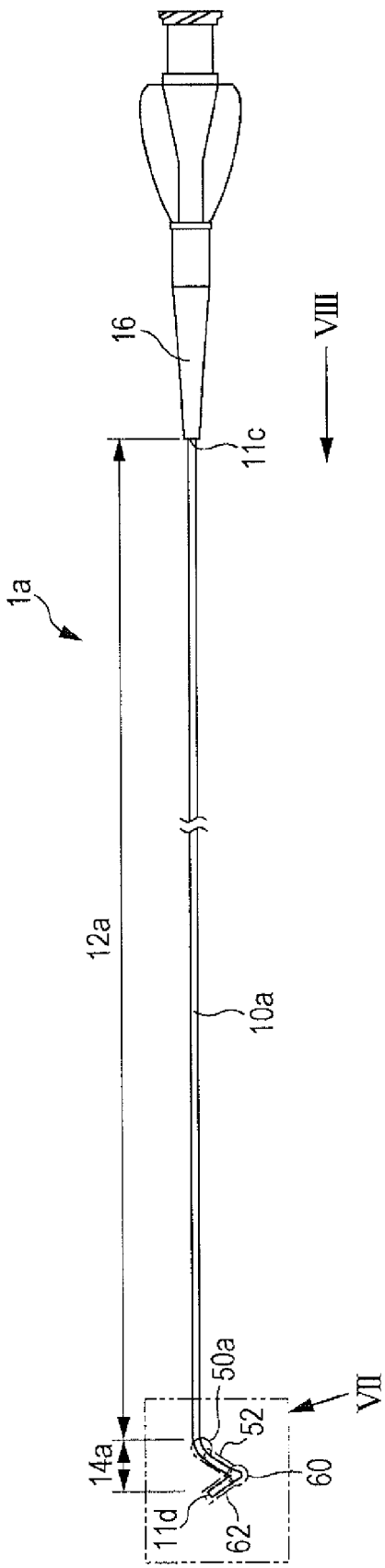

FIG. 6 illustrates a modification of the catheter of FIG. 1.

Figure 7:
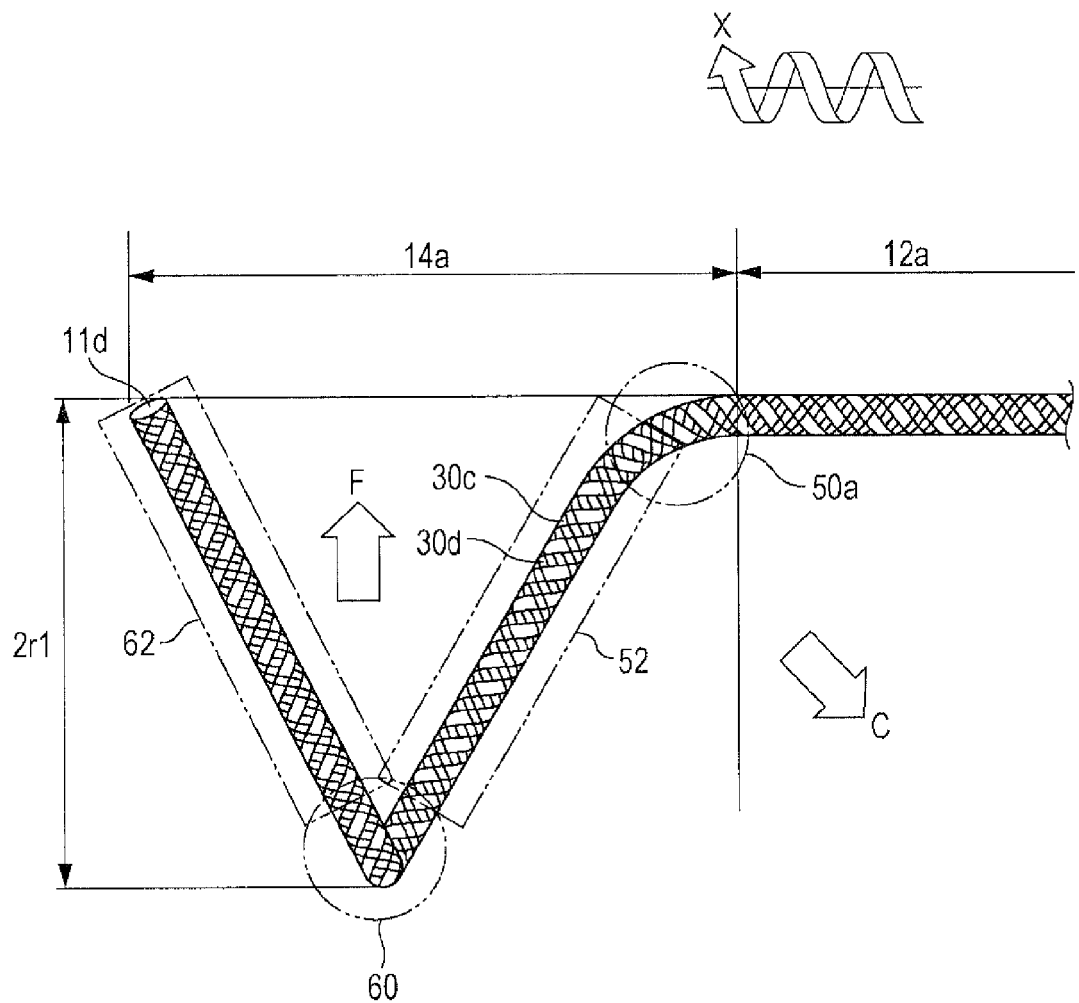

FIG. 7 is an enlarged diagram of portion VII of FIG. 6.

Figure 8:
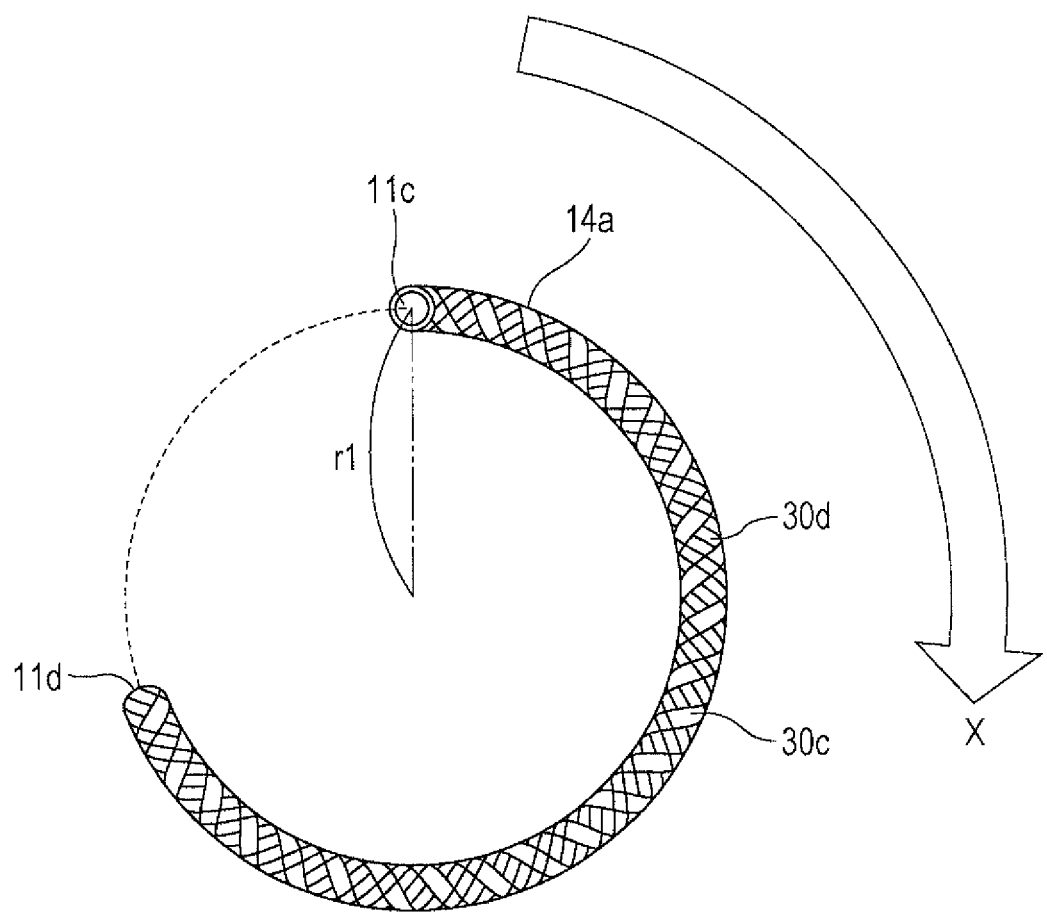
Figure 9:
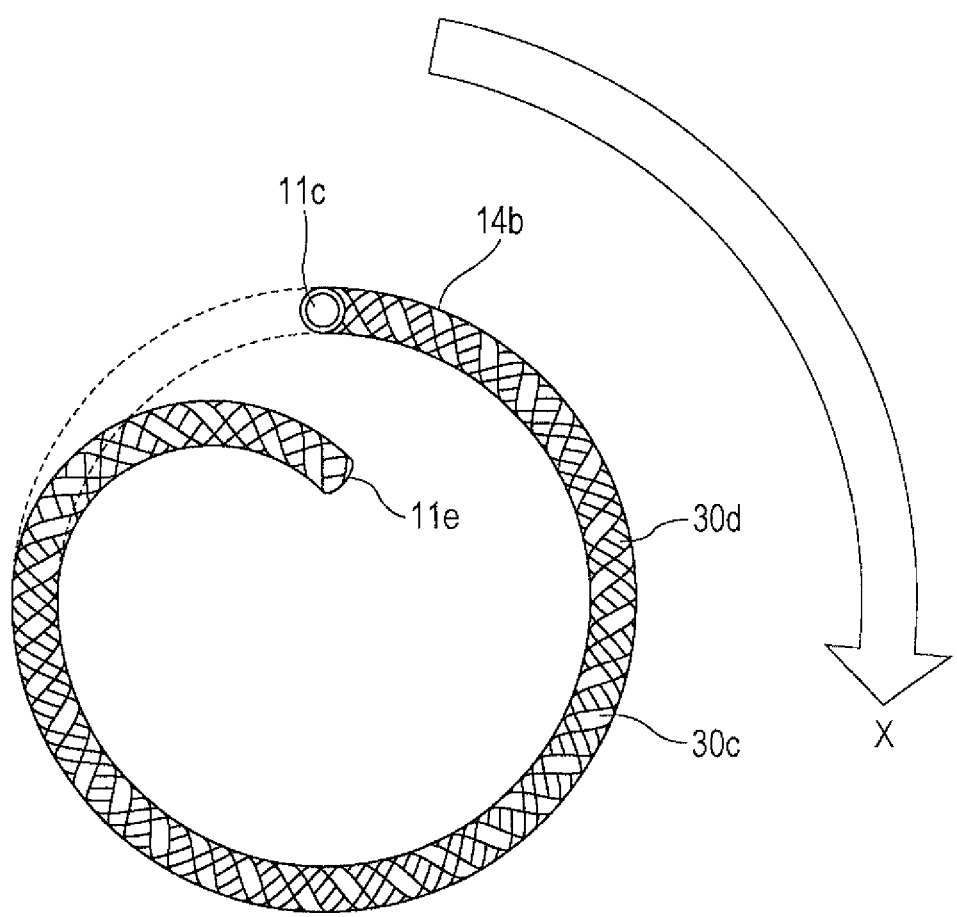

FIG. 8 is a diagram of the catheter shaft of FIG. 6 viewed from the proximal end of the catheter shaft, FIG. 9 is a diagram illustrating a modification of the catheter of FIG. 8.

Figure 10:
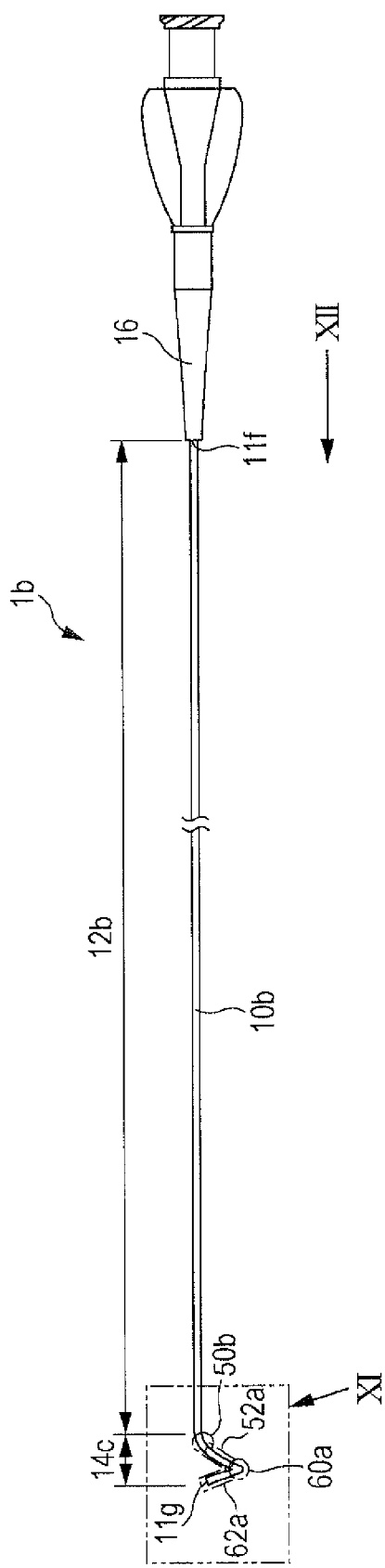

FIG. 10 illustrates a modification of the catheter of FIG. 6.

Figure 11:
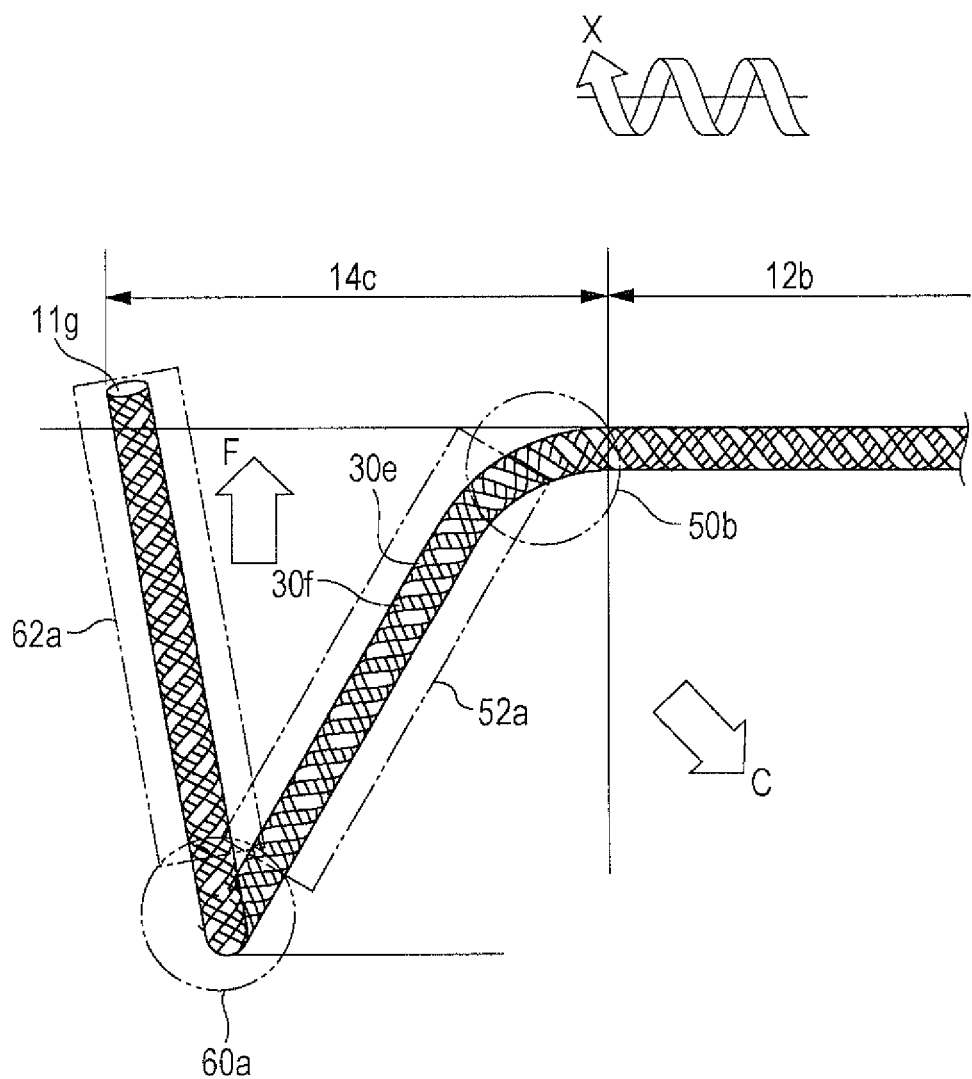

FIG. 11 is an enlarged diagram of portion XI of FIG. 10.

Figure 12:
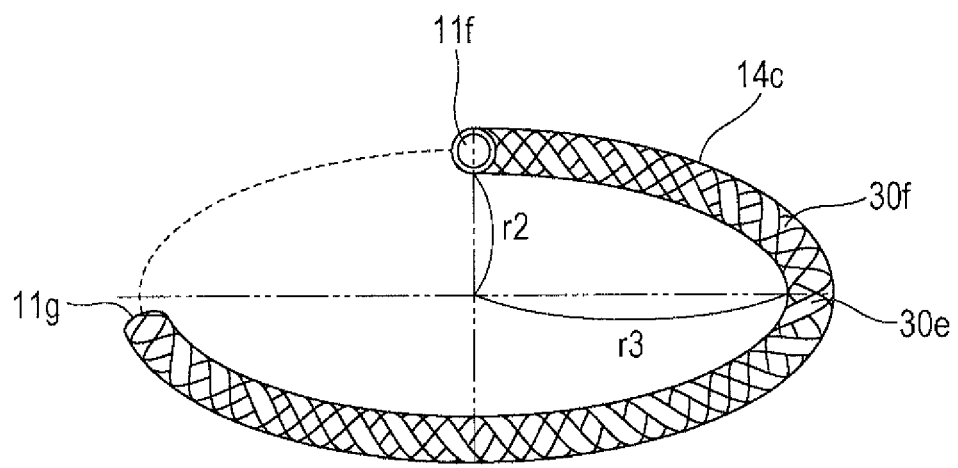

FIG. 12 is a diagram of the catheter shaft of FIG. 10 viewed from the proximal end of the catheter shaft.

FIGS. 13A to 13C are diagrams illustrating a manner in which the catheter changes in proceeding direction from a major canal to a minor canal.

DETAILED DESCRIPTION OF EMBODIMENTS

A catheter 1 of the disclosed embodiments will be described with reference to FIGS. 1 to 5. In FIGS. 1, 2, and 4, the left side of the drawing corresponds to a distal end of the catheter 1 to be inserted into the body, and the right side of the drawing corresponds to a proximal end of the catheter 1 which is to be manipulated by a technician, such as a doctor.

The catheter 1 is used to treat, for example, a stenosis site or an occlusion site that is formed in a blood vessel, a bile duct, a pancreatic duct, or the like. As illustrated in FIG. 1, the catheter 1 mainly includes a catheter shaft 10 including a proximal end 11a, a linear body portion 12, a bend 14, and a distal end 11b, as well as a connector 16 attached to the proximal end 11a of the catheter shaft 10.

As illustrated in FIGS. 2 and 3, the catheter shaft 10 includes, in a radial direction and in order from the inside of the catheter shaft 10, an inner layer 20, a braid 30 as a reinforcement body, and an outer layer 40. Note that although FIG. 2 is an illustration of the catheter shaft 10, a portion of the braid 30 and a portion of the outer layer 40 have been removed for convenience of description. FIG. 3 is a cross-sectional view taken along line III-III of FIG. 2.

The inner layer 20 is formed of resin and includes a lumen 22 for inserting a guide wire or another catheter therein. The resin material forming the inner layer 20 is not limited to a particular material; however, when considering the sliding property of the guide wire or the catheter that is to be inserted inside the inner layer 20, the resin material is desirably polytetrafluoroethylene (PTFE).

The braid 30 is formed on the outer periphery of the inner layer 20 as a reinforcement body. The braid 30 is a member in which a first wire 30a having a high tensile strength and a second wire 30b having a low tensile strength are woven into a net-like form (a mesh-like form). When viewed in a V-direction of FIG. 1 from the proximal end 11a of the catheter shaft 10, the first wire 30a is wound in the clockwise direction (right-hand direction) and the second wire 30b is wound in the counterclockwise direction (left-hand direction), and the first wire 30a and the second wire 30b are alternately woven together (see FIG. 2).

The materials of the first wire 30a and the second wire 30b constituting the braid 30 may be the same, or different materials may be used. In either case, the tensile strength of the first wire 30a should be higher than the tensile strength of the second wire 30b. In the catheters of FIGS. 1 to 5, the same metal material (e.g., stainless steel (SUS316)) is used in the first wire 30a and the second wire 30b, and the wire diameter of the first wire 30a is large and the wire diameter of the second wire 30b is small (see FIG. 3). However, the method of making the tensile strength of the first wire 30a higher than the tensile strength of the second wire 30b is not limited to the above method. For example, when the first wire 30a and the second wire 30b are formed of the same material, the tensile strength of the first wire 30a and the second wire 30b can be adjusted by modifying the number of wires stranded to form each of the first wire 30a and the second wire 30b. Furthermore, when the first wire 30a and the second wire 30b are formed with the same wire diameter, a material with a high tensile strength (tungsten, for example) may be used in the first wire 30a to impart a high tensile strength, and a material with a low tensile strength (stainless steel (SUS316), for example) may be used in the second wire 30b to impart a low tensile strength. Note that the materials of the first wire 30a and the second wire 30b are not limited to metal and may be, for example, carbon fiber or reinforced fiberglass.

Furthermore, although the cross-sectional shapes of the first wire 30a and the second wire 30b are both round in FIG. 3, the cross-sectional shapes are not limited to the above shapes. For example, the cross-sectional shape of the first wire 30a may be rectangular and the cross-sectional shape of the second wire 30b may be round.

The outer layer 40 formed of resin that is formed on the outer periphery of the braid 30 covers the inner layer 20 and the braid 30. The resin material forming the outer layer 40 is not limited to a particular material and may be, for example, a polyamide, polyamide elastomer, polyester, or polyurethane.

Although FIG. 4 is an enlarged view of portion IV of FIG. 1, for convenience of description, the outer layer 40 that covers the catheter shaft 10 is removed such that FIG. 4 illustrates the braid 30 in which the first wire 30a and the second wire 30b are woven together. As illustrated in FIG. 4, the bend 14 extends from the body portion 12 to the distal end of the catheter shaft 10 and is tilted from the body portion 12 through the first bend 50 that is bent in a first direction C. A winding direction X of the first wire 30a embedded in the catheter shaft 10 is the clockwise direction.

FIG. 5 is a diagram of the catheter shaft 10 when viewed from the proximal end 11a of the catheter shaft 10 in the V-direction of FIG. 1. Similar to FIG. 4, for convenience of description, the outer layer 40 that covers the catheter shaft 10 is removed such that the braid 30 in which the first wire 30a and the second wire 30b are woven together is illustrated. As illustrated in FIG. 5, when viewed in the V-direction of FIG. 1 from the proximal end 11a of the catheter shaft 10, the bend 14 forms an arc with a radius of r1 extending in the clockwise direction (i.e., in the winding direction X of the first wire 30a). In other words, when viewed in the V-direction of FIG. 1 from the proximal end 11a of the catheter shaft 10, the entire catheter shaft 10 from the proximal end 11a to the distal end 11b aligns along a circumference with a radius of r1.

As described above, the tensile strength of the first wire 30a is higher than the tensile strength of the second wire 30b in the catheter 1. When the technician rotates the catheter 1 in the clockwise direction (which is the same direction as the winding direction X of the first wire 30a), the properties of the braid 30 are governed by the first wire 30a, which functions as a coil. Accordingly, even when the distal end of the catheter 1 is caught by a portion around the entrance of a minor canal at a bifurcation, the technician can deform the bend of the catheter shaft into a thin state by rotating the catheter 1 in the clockwise direction, thereby tightening the first wire 30a. Accordingly, it is easy to change the proceeding direction of the catheter 1 from a major canal to a minor canal, and the amount of time taken to insert the catheter 1 into a stenosis site or an occlusion site formed at an end portion of a tubular organ can be reduced.

A modification of the catheter 1 of FIG. 1 will be described with reference to FIGS. 6 to 9. In FIGS. 6 and 7, the left side of the drawing corresponds to a distal end of the catheter 1a which is to be inserted into the body, and the right side of the drawing corresponds to a proximal end of the catheter 1a which is to be manipulated by a technician, such as a doctor.

Only differences from the catheter 1 illustrated in FIGS. 1 to 5 will be described. As illustrated in FIG. 6 and FIG. 7 (an enlarged drawing of a portion VII of FIG. 6), a bend 14a in the catheter 1a extends from the body portion 12a towards the distal end. The bend 14a includes a first tilted portion 52 that extends obliquely relative to the body portion 12a through the first bend 50a that is bent in a first direction C, and a second tilted portion 62 that is tilted from the first tilted portion 52 and that extends distally through a second bend 60 that is bent in a second direction F that is a direction different from the first direction C. Similar to FIG. 4, the winding direction X of a first wire 30c embedded in the catheter shaft 10a is the clockwise direction. Meanwhile, a second wire 30d that is embedded in the catheter shaft 10a is wound in the counterclockwise direction.

FIG. 8 is a diagram of the catheter shaft 10a when viewed from a proximal end 11c of the catheter shaft 10a in the VIII-direction of FIG. 6. As illustrated in FIG. 8, when viewed in the VIII-direction of FIG. 6 from the proximal end 11c of the catheter shaft 10a, the bend 14a forms an arc with a radius of r1 extending in the clockwise direction, which is the winding direction X of the first wire 30c. In other words, when viewed in the VIII-direction of FIG. 6 from the proximal end 11c of the catheter shaft 10a, the entire catheter shaft 10a from the proximal end 11c to a distal end 11d aligns along a circumference with a radius of r1.

Compared with the catheter 1, in the catheter 1a, the length of the first wire 30c that functions as a coil in the bend 14a is longer (see FIGS. 5 and 8). In the bend 14a, since the first wire 30c that functions as a coil is long, the bend 14a can be easily deformed into a thin state when the technician rotates the catheter 1a in the clockwise direction, which is the same direction as the winding direction X of the first wire 30c. Furthermore, since the second tilted portion 62 extends in the distal direction, when the distal end of the catheter 1a is caught by a portion around the entrance of the minor canal (the side branch) at a bifurcation, the technician can simultaneously rotate the catheter 1a in the clockwise direction (deforming the bend 14a into a thin state), and push the distal end of the catheter 1a so as to transmit a pushing force to the distal end of the catheter 1a while the bend 14a is deformed in the thin state. Accordingly, the catheter 1a can be easily guided into the minor canal without the distal end of the catheter 1a being caught again by a portion around the entrance of the minor canal (the side branch).

As illustrated in FIG. 9, a bend 14b of the catheter shaft 10a may have an arc that is longer than a circumference of a circle having a radius of r1 (i.e., longer than a single lap around the circumference) when viewed in the VIII-direction of FIG. 6 from the proximal end 11c of the catheter shaft 10a. In this manner, the length of the first wire 30c that functions as a coil in the bend 14b can be extended further. Note that in FIG. 9, in order to facilitate understanding, a distal end 11e of the catheter shaft 10a is illustrated at a displaced position with respect to the circumference with a radius of r1; however, the position of the distal end 11e of the catheter shaft 10a is not limited to the above position. As in FIG. 8, the distal end 11e of the catheter shaft 10a may be positioned on the circumference with a radius of r1.

A modification of the catheter 1a of FIG. 6 will be described with reference to FIGS. 10 to 12. In FIGS. 10 and 11, the left side of the drawing corresponds to a distal end of the catheter 1b to be inserted into the body, and the right side of the drawing corresponds to a proximal end of the catheter 1b which is to be manipulated by the technician, such as a doctor.

Only differences from the catheter 1a illustrated in FIGS. 6 to 9 will be described. As illustrated in FIG. 10 and FIG. 11 (which is an enlarged drawing of a portion XI of FIG. 10), a bend 14c in the catheter 1b extends from the body portion 12b towards the distal end. The bend 140 includes a first tilted portion 52a that extends obliquely relative to the body portion 12b through a first bend 50b that is bent in the first direction C, and a second tilted portion 62a that is tilted from the first tilted portion 52a and that extends distally through a second bend 60a that is bent in a second direction F that is a direction different from the first direction C. As in FIG. 7, the winding direction X of a first wire 30e embedded in the catheter shaft 10b is the clockwise direction. Meanwhile, a second wire 30f that is embedded in the catheter shaft 10b is wound in the counterclockwise direction.

FIG. 12 is a diagram of the catheter shaft 10b when viewed from a proximal end 11f of the catheter shaft 10b in the XII-direction of FIG. 10. As illustrated in FIG. 12, when viewed in the XII-direction of FIG. 10 from the proximal end 11f of the catheter shaft 10b, the bend 14c forms an arc extending in the clockwise direction, which is the winding direction X of the first wire 30e. However, unlike in FIG. 8, the arc is an ellipse with a minor axis of r2. In other words, when viewed in the XII-direction of FIG. 10 from the proximal end 11f of the catheter shaft 10b, the entire catheter shaft 10b from the proximal end 11f to a distal end 11g aligns along a circumference of the ellipse with the minor axis of r2 and a major axis of r3.

Compared with the catheter 1a, the second bend 60a of catheter 1b is bent in a sharp manner (at a very acute angle) with respect to the first tilted portion 52a and forms an apex. That is, the second bend 60a is bent at a more acute angle than the second bend 60 and forms a point (an apex) that abuts against the wall of the major canal during use. When the apex of the second bend 60a is abutted against the wall of the major canal, the second bend 60a acts as a fulcrum and the rotational force of the technician is easily transmitted to the distal end of the catheter 1b. As a result, the proceeding direction of the catheter 1b can be changed from the major canal to the minor canal in an easier manner.

Referring next to FIGS. 13A to 13C, a manlier in which the catheter 1, 1a, or 1b changes the proceeding direction from a major canal (a main branch) 70 to a minor canal (a side branch) 80 will be described. For convenience of description, the catheter 1a is shown in FIGS. 13A to 13C; however, the same process can be performed with the catheters 1 and 1b.

FIG. 13A is a diagram that illustrates a state in which the distal end of the catheter 1a is caught by a portion around an entrance 82 of the minor canal 80. The bend 14a of the catheter shaft 10a forms the arc with a radius of r1 extending in the clockwise direction (which is the winding direction X of the first wire 30c having a high tensile strength). At this time, the width of the bend 14a is at most r1×2=2r1 (see FIG. 7). FIG. 13B is a diagram that illustrates a state in which the technician has rotated the catheter 1a in the clockwise direction. In the bend 14a of the catheter shaft 10a, the first wire 30c functions as a coil and rotates while being tightened so as to deform the bend 14a into a thin state. Accordingly, the distal end of the catheter 1a that had been caught is moved away from the portion around the entrance 82 of the minor canal 80. At this time, the width of the bend 14a is r4, which is smaller than 2r1 (r4<2r1). In the above state, when the technician pushes the catheter 1a in a distal end direction Y, as illustrated in FIG. 13C, the proceeding direction can be changed from the major canal 70 to the minor canal 80 without the distal end of the catheter 1a being caught again by a portion around the entrance 82 of the minor canal 80.

Note that in the above description, although the winding direction X of the first wires 30a, 30c, and 30e constituting the braid 30 of the catheters 1, 1a, and 1b, respectively, is the clockwise direction, the winding direction X is not limited to the above. When the winding direction of the first wires 30a, 30c, and 30e is the counterclockwise direction, the bends 14, 14a, 14b, and 14c of the catheter shafts 10, 10a, and 10b form an arc extending in the counterclockwise direction when viewed in the V-direction of FIG. 1, the VIII-direction of FIG. 6, and the XII-direction of the FIG. 10 from the proximal ends 11a, 11c, and 11e of the catheter shafts 10, 10a, and 10b.

As described above, in the catheters 1, 1a, and 1b, the tensile strengths of each of the first wires 30a, 30c, and 30e are higher than the corresponding tensile strength of each of the second wires 30b, 30d, and 30f, respectively. Accordingly, even when the distal end of the catheter 1, 1a, or 1b is caught by a portion around the entrance 82 of the minor canal 80 at the bifurcation, the technician can deform the bend 14, 14a, or 14c of the catheter shaft 10, 10, or 10b into a thin state by rotating the catheter 1, 1a, or 1b in the winding direction X of the first wire 30a, 30c, or 30e, thereby tightening the first wire 30a, 30c, or 30e. Accordingly, it is easy to change the proceeding direction of the catheter 1, 1a, or 1b from the major canal 70 to the minor canal 80, and the amount of time taken to insert the catheter 1, 1a, or 1b into a stenosis site or a occlusion site formed at the end portion of the tubular portion can be reduced.

What is claimed is:

1. A catheter comprising:
a catheter shaft including:
a body portion, and
a bend that extends distally from a distal end of the body portion, wherein:
a braid is embedded in the catheter shaft, the braid having a first wire and a second wire woven together, the first wire having a high tensile strength and the second wire having a low tensile strength that is lower than the high tensile strength of the first wire, and
when viewed from a proximal end of the catheter shaft, the bend forms an arc that extends in a nonlinear winding direction of the first wire.

2. The catheter according to claim 1, wherein the bend includes:
a first tilted portion that extends obliquely relative to the body portion through a first bend that is bent in a first direction, and
a second tilted portion that is tilted relative to the first tilted portion and extends distally through a second bend that is bent in a second direction, the second direction being a direction that is different from the first direction.

3. The catheter according to claim 2, wherein the second bend is bent at an acute angle with respect to the first tilted portion, which is lesser than an angle at which the first bend is bent relative to the body portion.

4. The catheter according to claim 1, wherein when viewed from the proximal end of the catheter shaft, the bend forms an arc that extends along a circumference of a circle.

5. The catheter according to claim 1, wherein when viewed from the proximal end of the catheter shaft, the bend forms an arc that extends along a circumference of an ellipse.

6. The catheter according to claim 1, wherein the first wire has a thickness that is greater than a thickness of the second wire.

\* \* \* \* \*